(12) United States Patent
Subraya et al.

(10) Patent No.: US 10,978,268 B1
(45) Date of Patent: Apr. 13, 2021

(54) METHODS AND SYSTEMS FOR AN X-RAY TUBE ASSEMBLY

(71) Applicant: GE Precision Healthcare LLC, Milwaukee, WI (US)

(72) Inventors: Madhusudhana Subraya, New Berlin, WI (US); Richard Brogan, New Berlin, WI (US); Kalyan Koppisetty, Waukesha, WI (US); Donald Allen, Waukesha, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 16/670,935

(22) Filed: Oct. 31, 2019

(51) Int. Cl.
| | |
|---|---|
| *H01J 35/06* | (2006.01) |
| *H01J 35/16* | (2006.01) |
| *H05G 1/20* | (2006.01) |
| *H05G 1/26* | (2006.01) |
| *A61B 6/03* | (2006.01) |

(52) U.S. Cl.
CPC .......... *H01J 35/165* (2013.01); *H01J 35/064* (2019.05); *H05G 1/20* (2013.01); *H05G 1/26* (2013.01); *A61B 6/03* (2013.01); *H01J 2235/0233* (2013.01)

(58) Field of Classification Search
None
See application file for complete search history.

(56) References Cited

U.S. PATENT DOCUMENTS

| | | | | |
|---|---|---|---|---|
| 4,415,835 A | * | 11/1983 | Mishra | H01J 61/06 313/346 R |
| 4,487,589 A | * | 12/1984 | Mishra | H01J 61/06 445/51 |
| 5,627,871 A | | 5/1997 | Wang | |
| 6,438,207 B1 | * | 8/2002 | Chidester | H01J 35/14 378/138 |
| 6,973,158 B2 | | 12/2005 | Besson | |
| 7,834,321 B2 | | 11/2010 | Yorkston et al. | |
| 8,441,189 B2 | * | 5/2013 | Halfmann | H01J 61/34 313/607 |
| 8,824,637 B2 | * | 9/2014 | Morton | H01J 35/16 378/141 |
| 2003/0135971 A1 | | 7/2003 | Liberman et al. | |
| 2010/0327722 A1 | * | 12/2010 | Halfmann | H01J 61/34 313/1 |
| 2011/0222665 A1 | * | 9/2011 | Morton | H01J 35/165 378/141 |
| 2014/0342631 A1 | * | 11/2014 | Morton | H01J 35/165 445/28 |

* cited by examiner

*Primary Examiner* — Thomas R Artman
(74) *Attorney, Agent, or Firm* — McCoy Russell LLP

(57) ABSTRACT

Various systems are provided for an X-ray system. In one example, the X-ray system comprising a high-voltage connector physically coupled to a cathode of an X-ray tube via a plurality of pins, wherein the pins comprise niobium.

20 Claims, 6 Drawing Sheets

METHODS AND SYSTEMS FOR AN X-RAY TUBE ASSEMBLY

TECHNICAL FIELD

Embodiments of the subject matter disclosed herein relate to medical imaging and the facilitation of x-ray scanning.

DISCUSSION OF ART

In an x-ray tube, ionizing radiation is created by accelerating electrons in a vacuum from a cathode to an anode via an electric field. The electrons originate from a filament of a cathode assembly with current flowing therethrough. The filament may be driven by a high-frequency generator to liberate electrons from the cathode and accelerate the electrons toward the anode.

BRIEF DESCRIPTION

In one embodiment, an X-ray system comprises an interface configured to couple a high-voltage connector to an X-ray tube via a pin comprising a refractory material.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
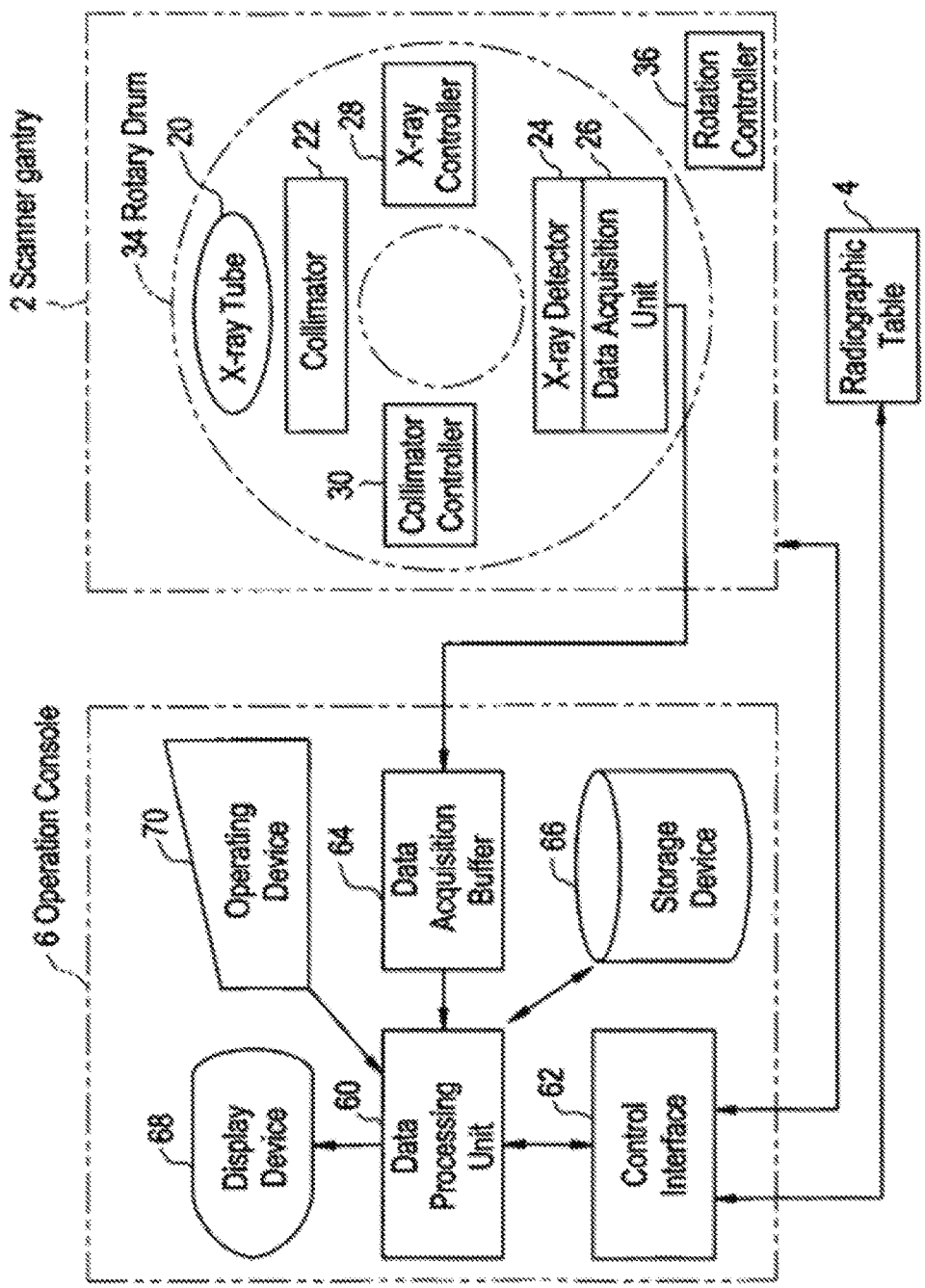
FIG. 1 shows a block diagram of an X-ray system.
Figure 2A:
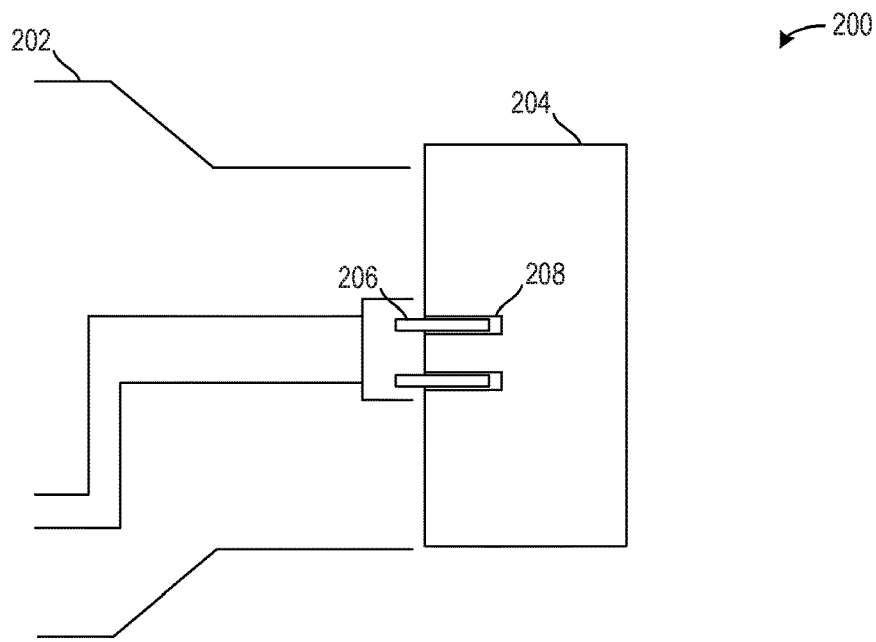
FIGS. 2A and 2B show a high-voltage connector with a plurality of pins for coupling the high-voltage connector to an x-ray tube of the X-ray system.
Figure 2B:
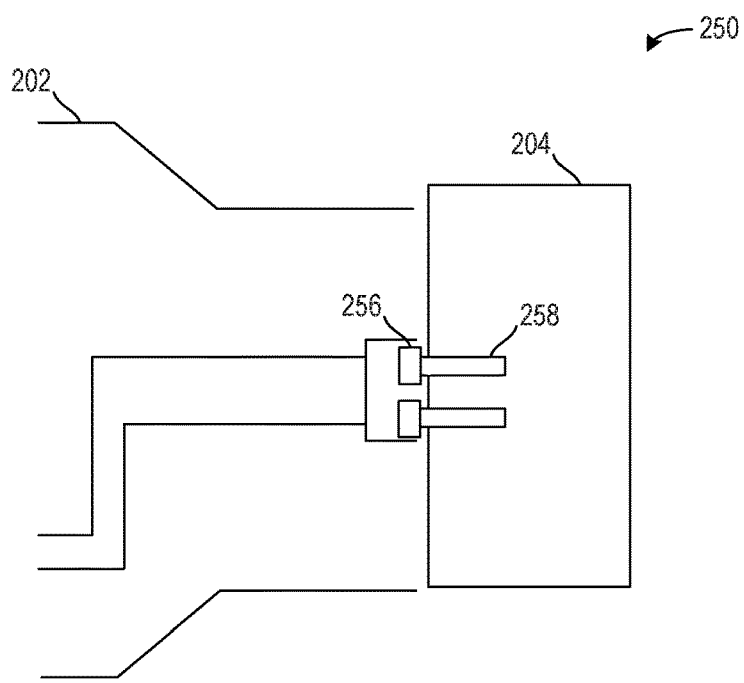
Figure 2C:
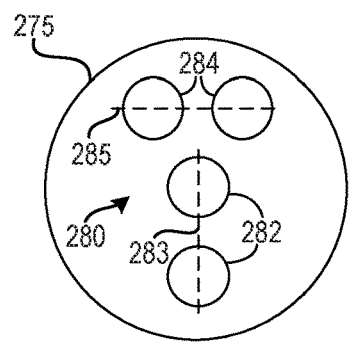
FIG. 2C illustrates an example arrangement of pins for physically coupling the high-voltage connector to a minor insulator assembly.
Figure 3A:
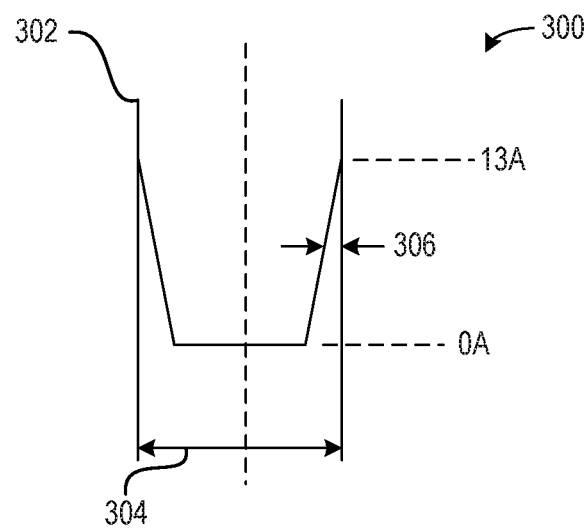
FIG. 3A shows skin depth of a previous example of pins comprising Kovar.
Figure 3B:
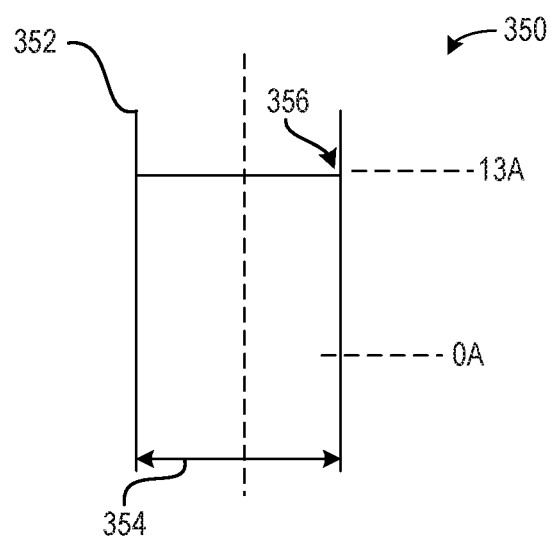
FIG. 3B shows a skin depth of a present example of pins comprising a refractory material.
Figure 4A:
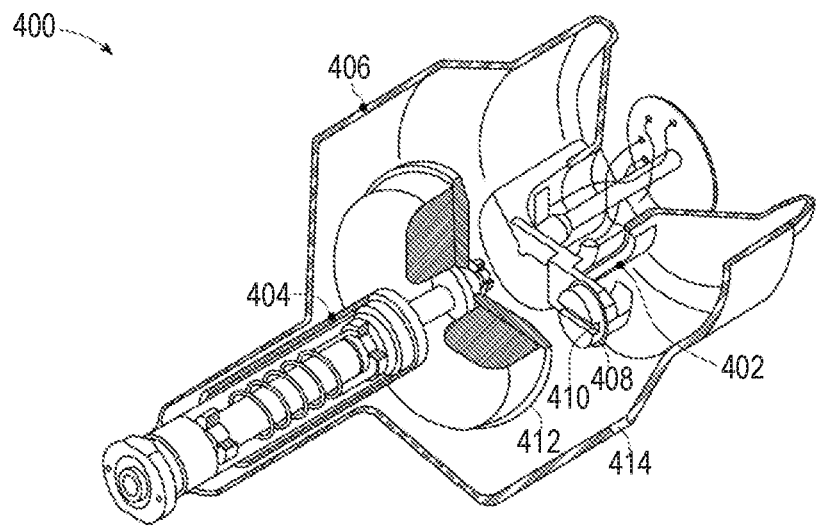
FIGS. 4A and 4B illustrate an X-ray tube assembly and detailed flat emitter assembly, respectively.
Figure 4B:
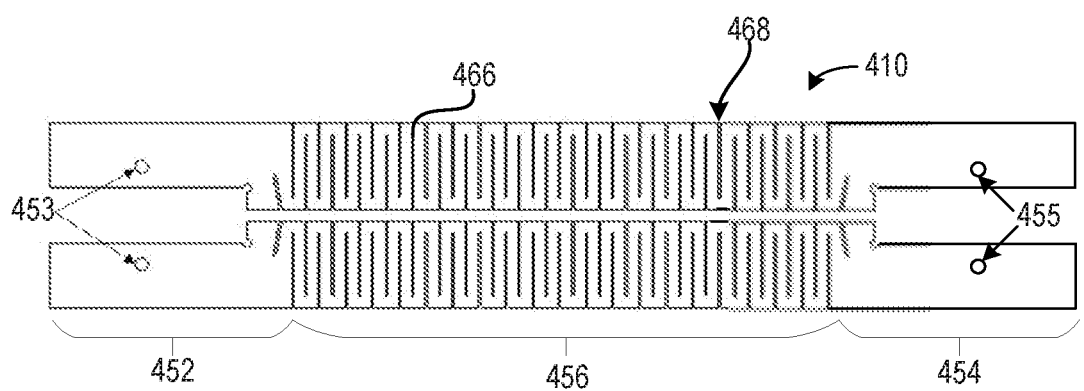

The following description relates to embodiments of a minor insulator for an X-ray tube. FIG. 1 illustrates an example block diagram of an X-ray system. FIGS. 2A and 2B illustrate example pin and socket arrangements. FIG. 2C illustrates an example pin orientation for a minor insulator assembly. FIG. 3A illustrates a skin depth of a previous example of pins used to physically couple a high-voltage connector to a cathode. FIG. 3B illustrates a skin depth of a present example of pins used to physically coupled the high-voltage connector to the cathode. FIG. 3C illustrates an example orientation of pins used to physically coupled the high-voltage connector to the cathode tube. FIG. 4A illustrates a detailed view of the X-ray tube. FIG. 4B illustrates a detailed via of the flat emitter arranged in the X-ray tube. FIGS. 5A, 5B, 5C, and 5D illustrate different pin materials and brazing techniques to reduce thermal transfer to the pins and the components surrounding the pins.

FIGS. 2A to 5D show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Turning to FIG. 1, it shows an X-ray CT system 1 comprising a scanner gantry 2, a radiographic table 4, and an operation console 6. The scanner gantry 2 includes an X-ray tube 20. X-rays radiated from the X-ray tube 20 are recomposed or collimated into a conical X-ray beam or a cone beam X-radiation by a collimator 22, and then irradiated to an X-ray detector 24. The assembly of the X-ray tube 20 and collimator 22 is an example of an X-ray generating device included in the present disclosure.

The X-ray detector 24 includes a plurality of detector elements arranged in a two-dimensional array along with the spread of a cone beam X-radiation. A subject of radiography is carried into a space between the X-ray tube 20 and X-ray detector 24 while lying down on the radiographic table 4.

The X-ray tube 20 has a plurality of focal spots and generates X-ray beams from the focal spots. The collimator 22 collimates the plurality of X-radiations. The X-ray tube 20, collimator 22, and X-ray detector 24 constitute X-irradiation/detection equipment.

A data acquisition unit 26 is connected to the X-ray detector 24. The data acquisition unit 26 acquires detection signals, which are sent from the respective detector elements included in the X-ray detector 24, in the form of digital data. The X-ray detector 24 and data acquisition unit 26 constitute an example of an acquiring means included in the present disclosure. The detection signals sent from the detector elements serve as a signal representing a projection of a subject produced with X-rays.

X-irradiation from the X-ray tube 20 is controlled by an X-ray controller 28. The illustration of the coupling between the X-ray tube 20 and X-ray controller 28 will be described in greater detail below. The X-ray controller 28 may comprise a high-frequency current drive circuit. Additionally or alternatively, a high voltage generator, which may be included in the X-ray controller 28, may comprise the high-frequency current drive circuit. A high voltage connector may carry the voltage and emitter current generated by the high-voltage generator to the X-ray tube 20. The voltage and emitter current may free electrons from an electron emission source of a cathode of the X-ray tube 20, wherein the electron source may be a coiled filament or a flat emitter with a larger emission area for increased emission current. However, to utilize the larger emission area of the flat emitter, the X-ray tube may demand higher voltages and emitter currents, resulting in increased heat dissipated into components of the X-ray tube 20, the X-ray controller 28, and the interface/coupling between the high-voltage connector and the X-ray tube 20. Embodiments of the interface/coupling to more efficiently dissipate heat are described below. The collimator 22 is controlled by a collimator controller 30. The illustration of the coupling between the collimator 22 and collimator controller 30 will be omitted.

The foregoing components starting with the X-ray tube 20 and ending with the collimator controller 30 may be incorporated in a rotary drum 34 included in the scanner gantry 2, and can be rotated about a subject of radiography. The rotation of the rotary drum 34 is controlled by a rotation controller 36. The illustration of the coupling between the rotary drum 34 and rotation controller 36 will be omitted.

The operator console 6 includes a data processing unit 60. The data processing unit 60 is realized with, for example, a computer. A control interface 62 is connected to the data processing unit 60. The scanner gantry 2 and radiographic table 4 are connected to the control interface 62. The data processing unit 60 controls the scanner gantry 2 and radiographic table 4 via the control interface 62.

The data acquisition unit 26, X-ray controller 28, collimator controller 30, and rotation controller 36 incorporated in the scanner gantry 2 are controlled via the control interface 62, whereby a subject of radiography is scanned. The illustration of the connections of these components to the control interface 62 will be omitted. In one example, the data processing unit 60 comprises non-transitory memory with instructions stored thereon that enable the data processing unit 60 to signal to the X-ray controller 28 to activate the X-ray tube 20 by delivering voltage thereto.

A data acquisition buffer 64 is connected to the data processing unit 60. The data acquisition unit 26 incorporated in the scanner gantry 2 is connected to the data acquisition buffer 64. Data acquired by the data acquisition unit 26 is transferred to the data processing unit 60 via the data acquisition buffer 64.

A storage device 66 is connected to the data processing unit 60. Projection data transferred to the data processing unit 60 via the data acquisition buffer 64 and control interface 62 is stored in the storage device 66. Moreover, programs for giving instructions to the data processing unit 60 are stored in the storage device 66. The data processing unit 60 runs any of the programs, whereby an action is performed in the X-ray system 1.

The data processing unit 60 reconstructs an image using a plurality of views of projection data that is stored in the storage device 66 via the data acquisition buffer 64. The data processing unit 60 is an example of a reconstructing device included in the present disclosure.

A display device 68 and an operating device 70 are connected to the data processing unit 60. The display device 68 is realized with a graphic display or the like. The operating device 70 is realized with a keyboard having a pointing device.

A reconstructed image sent from the data processing unit 60 and other information are displayed on the display device 68. A user manipulates the operating unit 70 so as to enter various instructions or pieces of information that are transmitted to the data processing unit 60. The user uses the display device 68 and operating device 70 to interactively operate the X-ray CT system.

In the example of the present disclosure, a flat-emitter is utilized in the X-ray tube to utilize greater amounts of current from the high-voltage connector. By doing so, a Joule heating of various components arranged proximally to a cathode and a high-voltage connector may be increased relative to previous examples where a generator used provided a lower current, which may have been in the configuration of a direct current sent to a helical emitter. One example component which may be heated includes at least one pin used to physically couple the high-voltage connector to the cathode. The pin may be configured to conduct current from the high-voltage connector to the cathode, and in doing so may be heated. This heat may disperse through a minor insulator, wherein components proximal to the pin may also be heated. As will be described herein, by adjusting a material of the pin, Joule heating may be reduced while still providing the flat emitter with a desired amount of current for high-quality X-ray imaging via the X-ray assembly.

Turning now to FIGS. 2A and 2B, they show embodiments 200 and 250, respectively, of example interfaces between a high-voltage connector 204 and a cathode 202. In one example, the cathode 202 is included in the X-ray tube 20 of FIG. 1 and the high-voltage connector 204 interfaces between the X-ray tube 20 and the X-ray controller 28 of FIG. 1.

In one example, the high-voltage connector 204 drives a filament arranged in the cathode 202 via a relatively high frequency. For example, the relatively high frequency may be approximately 20-80 kHz. Due to the fact that a flat emitter is used high current is desired. The combination of high frequency and high drive current may cause a high resistive heat load. As these technologies advance, heat generated by the high-voltage connector 204 may increase as the frequency delivered to the cathode 202 increases. Components used in the interface to couple the HV connector 204 and the cathode 202 may be susceptible to heating, which may result in undesired heat transfer to other region of an X-ray system and/or degradation of the components.

Embodiment 200 of FIG. 2A illustrates a plurality of pins 206 inserted through corresponding sockets of a plurality of sockets 208. Each pin of the plurality of pins 206 may extend through a portion of a corresponding socket of the plurality of sockets 208. Embodiment 250 of FIG. 2B illustrates a plurality of sockets 256 physically coupled to a plurality of pins 258, wherein the plurality of pins 258 extend from the high-voltage connector 204 toward the cathode 202. In this way, the plurality of sockets 256 are arranged in a vacuum filled portion of the cathode 202 and the plurality of pins 258 extend from an air side corresponding to the high-voltage connector 204 to the vacuum filled portion comprising the plurality of sockets 256.

At any rate, in each of the embodiment 200 and the embodiment 250, the interface, which includes one or more of the plurality of pins 206, the plurality of sockets 208, the first plurality of pins 256, and the second plurality of pins 258, may comprise a refractory material. In one example, the refractory material may comprise a large skin depth, which is elaborated in FIG. 3C. By utilizing a refractory material with a large skin depth at high frequencies, a lower AC resistive heating may be generated as current flows through a larger portion of a pin cross-sectional area. In this way, the plurality of pins 206 of the present disclosure along with the plurality of sockets 208 provide an arrangement configured to allow higher currents to be delivered to the cathode 202 while mitigating a likelihood of degradation of the high voltage connector 204.

Turning now to FIG. 2C, it shows a minor insulator assembly 275 comprising a plurality of pins 280. The plurality of pins 280 may include one or more of the pins of FIGS. 2A and 2B. The plurality of pins 280 include exactly four pins, comprising a first pair of pins 282 and a second pair of pins 284. The first pair of pins 282 are aligned along a first axis 283 and the second pair of pins 284 are aligned along a second axis 285, wherein the second axis 285 is perpendicular to the first axis 283. It will be appreciated that the plurality of pins 280 may comprise other numbers and arrangements of pins.

The minor insulator assembly 275 may house a cathode assembly and an anode assembly, such as those shown in FIG. 4A. As described above, the combination of the high-frequency AC current from the high-voltage connector to meet current demands of the flat-emitter assembly to release electrons may exacerbate heating of the pins and other proximal components. While this higher frequency may provide the improved image quality of an X-ray system comprising the minor insulator assembly 275, the heating may decrease a durability of pins used in previous X-ray systems which used lower currents. As such, the refractory material may at least partially solve this issue, as the refractory material may conduct the higher amounts of current while reducing Joule heating.

Turning now to FIGS. 3A and 3B, they show a previous example 300 and a current example 350, respectively, of pins arranged in a high voltage connector. FIG. 3A illustrates a skin depth of a material previously used in a pin 302 with an X-ray system, such as the X-ray system 1 of FIG. 1. The pin 302 may comprise Kovar, which is a nickel-cobalt ferrous alloy. A combination of the material of the pin 302 along with the high frequency from a high-voltage connector, such as the high-voltage connector 204 of FIG. 2A, resulting pin and socket temperatures exceeding threshold degradation temperatures.

The pin 302 with the Kovar material comprises a skin depth 306 of approximately 55 μm with a diameter of between 1.5 to 3 mm. Kovar is a highly conductive material with a relatively low-resistivity (e.g., 49E-8). This may result in Kovar comprising a relatively low skin depth at high AC frequencies (e.g., 50 kHz). As such, Joule heating during use of the X-ray system may result in the pin and socket temperatures rising to temperatures above the threshold degradation temperature. In one example, the threshold degradation temperature is equal to about 180° C. However, due to the material of the pin and the high frequency transferred to the cathode as is desired in the current state of the art, the pin and socket temperatures may reach temperatures above 240° C., higher than the threshold degradation temperature. This may decrease a longevity of the X-ray system, resulting in increased maintenance costs and reduced reliability.

Turning now to FIG. 3B, it shows a pin 352 sized identically to the pin 302 of FIG. 3A such that a diameter 354 is exactly equal to the diameter 304 of FIG. 3A. The pin 352 may be used similarly to the pin 302 such that the pin 352 is a pin of a plurality of pins used to physically couple a high voltage connector to a cathode. The pin 352 comprises a material different than the material of the pin 302 in the previous example. In one example, the pin 352 comprises a refractory material, such as Niobium. The refractory material of the pin 352 may provide several benefits including decreased pin and socket temperatures while delivering the high amounts of current to the cathode.

In one example, the pin 352 comprises a skin depth 356 greater than the skin depth 306 of the pin 302. The skin depth 356 may be close to (e.g., equal to) or greater than about 1 mm for a current flow at 50 kHz, which is over 18 times greater than the skin depth 306 of the pin 302. In one example, a ratio of a skin depth of the pin 352 to a pin radius is equal to or greater than 1. As such, Joule heating (e.g., AC resistive heating) associated with the 50 kHz AC current flow relative to the pin 302 is reduced since less of the current is forced to an outside of the pin 352 compared to the pin 302 of FIG. 3A. That is to say, the pin 352, which may comprise niobium, or another refractory material such as molybdenum and/or tungsten, comprises a greater skin depth than Kovar at high frequencies, resulting in lower AC resistive heating as the current is allowed to flow through a larger portion of a cross-section area of the pin 352 compared to the pin 302. In one example, the temperature of the pin 352 and socket are approximately 120 to 140° C., which is less than the threshold degradation temperature.

In one example, the refractory materials may not be widely use due to their relatively high-cost and difficulty to braze and/or coat. Furthermore, these materials may be low strength, relative to previously used material such as those used in pin 302. For example, niobium may be an expensive material to which it is difficult to weld. Niobium may further comprise a stable oxide layer, which may contribute to difficulties in brazing and coating niobium.

Turning now to FIG. 4A, a cross sectional view of an X-ray tube 400, in accordance with one embodiment of the present specification, is depicted. The X-ray tube 400 may be used for medical diagnostic examinations and may be a non-limiting example of the X-ray tube 20 of FIG. 1. In a presently contemplated configuration, the X-ray tube 400 includes a cathode assembly 402 and an anode assembly 404 that are disposed within an evacuated enclosure 406. That is to say, the enclosure may be under vacuum (e.g., low pressure). It may be noted that the X-ray tube 400 may include other components, and is not limited to the components shown in FIG. 4A. The evacuated enclosure 406 may be a vacuum chamber that is positioned within a housing of the X-ray tube 400. Further, the cathode assembly 402 includes a cathode cup 408 that is configured to emit electrons towards the anode assembly 404. Particularly, electric current is applied to an electron source, such as a flat emitter 410 in the cathode cup 408, which causes electrons to be produced by thermionic emission. The electric current may be applied by a high voltage connector, such as the high voltage connector 204 of FIGS. 2A and 2B, that is electrically coupled between a voltage source, such as the X-ray controller 28 of FIG. 1, and the cathode assembly 402.

Furthermore, the anode assembly 404 includes a rotary anode disc 412 and a stator (not shown). The stator is provided with a magnetic field to rotate the rotary anode disc 412. Also, the rotary anode disc 412 is positioned in the direction of emitted electrons to receive the electrons from the cathode cup 408. In one example, a copper base with a target surface having materials with high atomic numbers ("Z" numbers), such as rhodium, palladium, and/or tungsten, is employed in the rotary anode disc 412. It may be noted that a stationary anode may also be used instead of the rotary anode disc 412 in the X-ray tube 400.

During operation, the flat emitter 410 in the cathode cup 408 emits a beam of electrons that is accelerated towards the rotary anode disc 412 of the anode assembly 404 by applying a high voltage potential between the cathode assembly 402 and the anode assembly 404. These electrons impinge upon the rotary anode disc at a focal spot and release kinetic energy as electromagnetic radiation of very high frequency, i.e., X-rays. Particularly, the electrons are rapidly decelerated upon striking the rotary anode disc 412, and in the process, the X-rays are generated therefrom. These X-rays emanate in all directions from the rotary anode disc 412. A portion of these X-rays may pass through a window or X-ray port 414 of the evacuated enclosure 406 to exit the X-ray tube 400 and be utilized to interact in or on a material sample, patient, or other object.

Turning now to FIG. 4B, it shows a detailed view of the filament. In the example of FIG. 4B, the filament is illustrated as a flat emitter 410. In one example, the filament is only configured as the flat emitter 410 to achieve a higher radiation flux via a higher emitter drive current which may not be achieved in a helical filament. However, it will be appreciated by those of ordinary skill in the art that the filament 410 may comprise other configurations to achieve the higher radiation flux without departing from the scope of the present disclosure.

The flat emitter 410 may be arranged in the cathode cup 408 and may be configured to direct an electron beam toward the rotary anode disc 412. The flat emitter 410 may be a conductive strip that is divided into three sections, including a first section 452, a second section 454 identical to the first section, and a third section 456. The first section 452 and the second section 454 are arranged at opposite extreme ends of the flat emitter 410 with the third section arranged therebetween. The third section 456 may comprise a plurality of slits or cuts 466 that define a winding track 468.

The first section 452 and the second section 454 may be welded to the cathode cup 408. The first section 452 may comprise a first plurality of welds 453 and the second section 454 may comprise a second plurality of welds 455. In some examples additionally or alternatively, the first and second sections 452, 454 may be attached via brazings or other similar techniques without departing from the scope of the present disclosure.

Figure 5A:
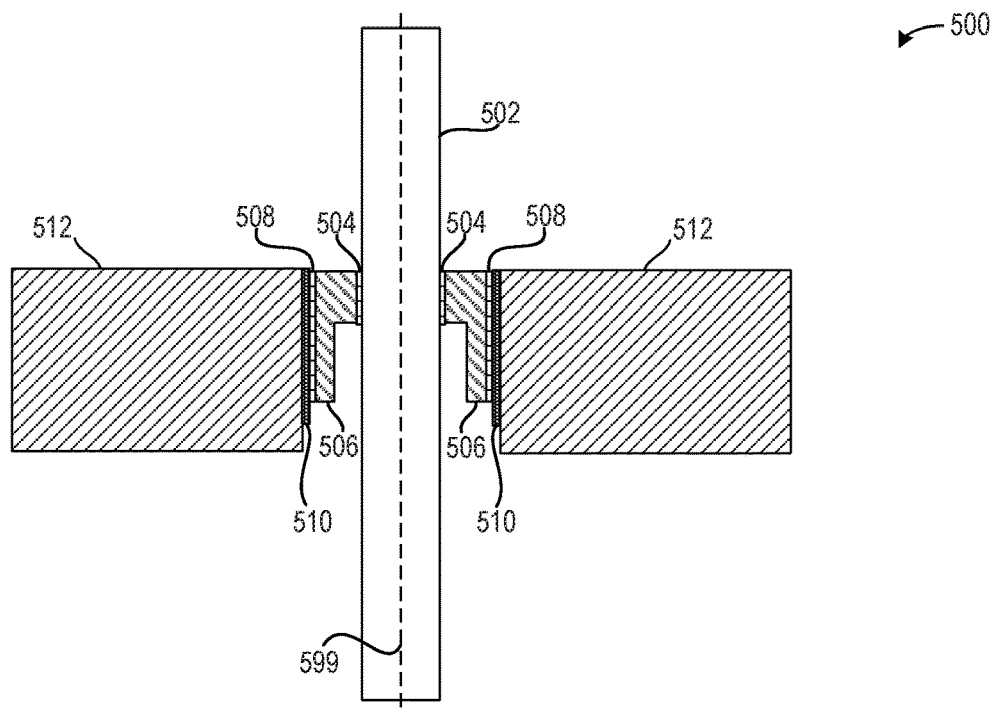
FIGS. 5A-5D show examples of a brazing included in various embodiments of the pins.

Turning now to FIG. 5A, it shows a cross-section of a first embodiment 500 of a brazed pin feedthrough. The first embodiment 500 comprises a pin 502, wherein the pin 502 may be used in the embodiments of FIGS. 2A and 2B and similarly to pin 352 of FIG. 3B.

The pin 502 comprises a first brazing 504 arranged between the pin 502 and a hat 506. A second brazing 508 may be arranged between the hat 506 and a metallization 510, wherein the metallization separates the second brazing 506 and a ceramic material 512. In one example, the ceramic material 512 may correspond to a material of a socket in which the pin is arranged.

The pin 502 may comprise a hat 506 due to a mismatch of thermal expansion values between the metal components, such as the pin 502 and the ceramic 512. Each of the first brazing 504, the hat 506, the second brazing 508, the metallization 510, and the ceramic material 512 extend around an entire circumference of the pin 502. The hat 506 may comprise a reduced wall thickness at an interface between the hat 506 and the second brazing 508, wherein a thickness is measured along an axis perpendicular to a central axis 599 of the pin 502. In one example, the first and/or second brazings 504, 508 may be higher temperature braze alloys relative to previously used brazings due to the stable oxide layer of the niobium pin 502.

In the example of FIG. 5A, the first embodiment 500 is symmetric. Moving in a direction away from the pin 502, the first brazing 504 and the hat 506 comprise identical widths at an interface therebetween, wherein the width is measured along an axis parallel to the central axis 599. As such, the hat 506 does not directly contact the pin 502. The hat 506 increases in width and decreases in thickness proximally to an interface between it and the second brazing 508, wherein the second brazing 508 does not contact the pin 502 due to the hat 506 and the first brazing 504. The metallization 510 comprises a width greater than a width of the second brazing 508. Additionally or alternatively, the wall thickness of the metallization 510 may be greater than a wall thickness of the second brazing 508. The ceramic material 512 may be a radially outermost portion of the first embodiment 500, wherein a width and a wall thickness of the ceramic material are greater than the width and wall thickness of each of the first brazing 504, the hat 506, the second brazing 508, and the metallization 510.

In one example, the hat 506 is a low expansion iron-nickel cobalt or iron-nickel alloy, wherein the pin 502 is uncoated (e.g., bare) and is directly brazed to the hat 506 via the first brazing 504. Due to the niobium pin 502 being uncoated, it may demand a braze alloy with a liquidus greater than approximately 900° C. to achieve wetting and braze flow. As such, the material of the first brazing 504 may be selected to achieve the desired wetting and braze flow. In one example, the first brazing comprises an alloy including one or more of a 50/50 mix of Au/Cu, 81.5/16.5 mix of Au/Cu (Nicoro-80), and 82/18 mix of Au/Cu (Nioro).

In one example, the first brazing 504 and the second brazing 508 may comprise identical materials. In another example, the first brazing 504 and the second brazing 508 may comprise different materials.

Additionally or alternatively, the pin 502 and the hat 506 may comprise different materials in the example of FIG. 5A. In one example, the pin 502 comprises one or more of niobium, tungsten, and molybdenum and the hat 506 comprises a nickel-cobalt ferrous alloy (e.g., Kovar). In one example, the first brazing 504 may be arranged between the pin 502 and the hat 506 to block formation of an intermetallic due to the reaction of niobium within one or more constituents of Kovar.

Figure 5B:
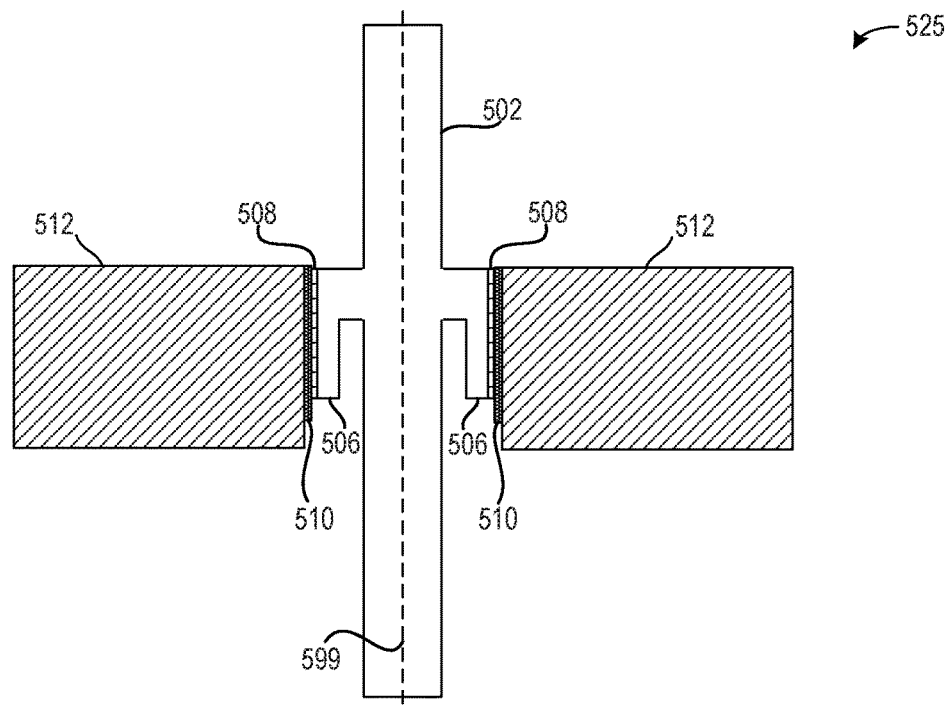

Turning now to FIG. 5B, it shows a second embodiment 525, which is substantially similar to the first embodiment 500, except that the pin 502 and the hat 506 are formed as a single, machined component (e.g., a monolith). As such, the pin 502 may be uncoated due to the omission of the first brazing (e.g., brazing 504 of FIG. 5A). The second brazing 508 in the example of FIG. 5B comprises a braze alloy of one or more of a 50/50 mix of Au/Cu, 81.5/16.5 mix of Au/Cu (Nicoro-80), and 82/18 mix of Au/Cu (Nioro).

Figure 5C:
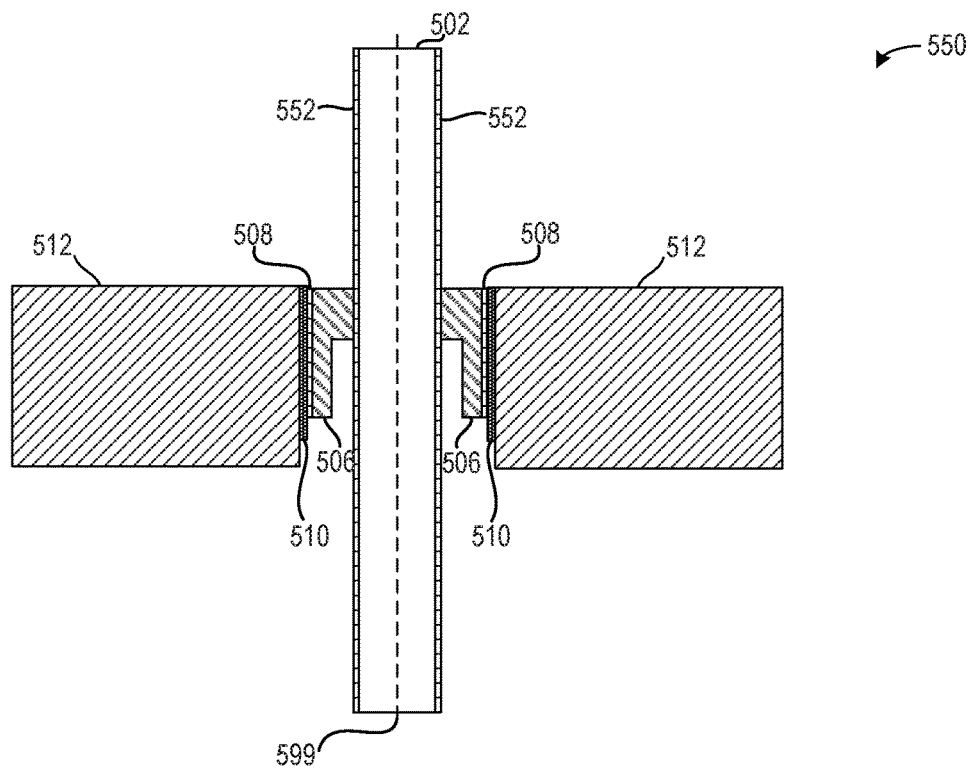

Turning now to FIG. 5C, it shows a third embodiment 550, which may be substantially similar to the first embodiment 500, except that the pin 502 is coated along its entire surface with a coating 552. The coating 552 may separate a material of the pin 502 (e.g., niobium) from a material of the hat 506 (e.g., Kovar). In one example, the pin 502 may react with Kovar via transport of material across a braze interface between the pin 502 and the hat 506. This transportation may result in a brittle intermetallic forming through the reaction of niobium (Nb) with one or more of iron (Fe), nickel (Ni), and cobalt (Co) in the Kovar. To block the formation of the intermetallic material, the pin 502 may be coated with the coating 552 comprising one or more of gold (Au) or platinum (Pt) with a coating thickness of about 1 to 10 microns. In the example of FIG. 5C, the coating 552 is gold. The coating 552 may enable enhanced wetting of the pin 502, thereby allowing incorporation of a lower temperature, lower cost braze material such as a 72/28 mix of Ag/Cu (Cusil). In this way, the second brazing 508 may comprise Cusil. In the example of FIG. 5C, the coating 552 comprises a width equal to the width of the pin 502 such that an entire surface of the pin 502 is coated with the coating 552. In some examples, additionally or alternatively, the coating 552 may only coat portions of the pin 502 that would otherwise directly contact the hat 506. By doing this, a manufacturing cost may be reduced.

Figure 5D:
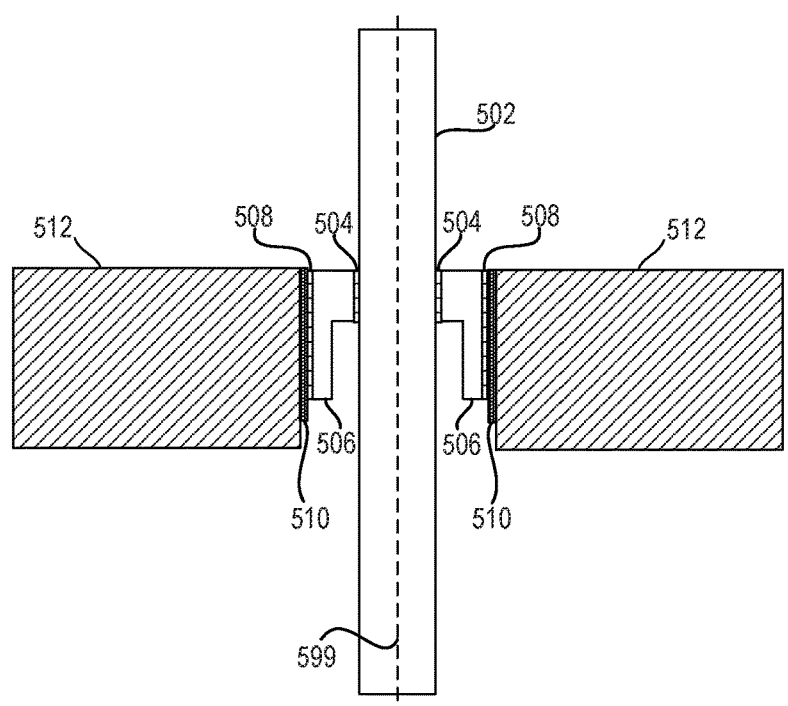

Turning now to FIG. 5D, it shows a fourth embodiment 575, which is substantially similar to the second embodiment 525 of FIG. 5B, except that the pin 502 and the hat 506 are machined as separate pieces. As such, the first brazing 504 is arranged between the pin 502 and the hat 506, even though each of the pin 502 and the hat 506 comprise niobium. The first brazing 504 may comprise one or more of a 50/50 mix of Au/Cu, 81.5/16.5 mix of Au/Cu (Nicoro-80), and 82/18 mix of Au/Cu (Nioro).

In one aspect, a high-voltage connector may comprise a plurality of pins configured to physically couple the high-voltage connector to an X-ray tube. The plurality of pins is configured to conduct high amounts of current from the high-voltage connector to a flat emitter, enabling increased image quality of the X-ray system. The plurality of pins may comprise a refractory material, such as niobium. The technical effect of the plurality of pins comprising the refractory material is to decrease a Joule heating resulting from the increased amount of current delivered to the flat emitter. By decreasing the Joule heating, a temperature of the pins and surrounding components may be reduced, thereby increasing their longevity and durability.

In one embodiment, an X-ray system comprises an interface configured to couple a high-voltage connector to an X-ray tube via a pin comprising a refractory material.

A first example of the X-ray system further comprises where the refractory material is one or more of niobium, molybdenum, and tungsten.

A second example of the X-ray system, optionally including the first example, further includes where the pin is arranged in a brazed vacuum feedthrough, wherein the pin comprises a hat formed as a single-piece monolith with the pin, wherein the pin and the hat comprise the refractory material.

A third example of the X-ray system, optionally including one or more of the previous examples, further includes where the pin is coated with a coating comprising gold or platinum, and wherein the coating separates the pin from a hat, wherein the hat comprises a nickel-cobalt ferrous alloy or a nickel-ferrous alloy.

A fourth example of the X-ray system, optionally including one or more of the previous examples, further includes where a ratio of a skin depth of the pin to a pin radius is equal to or greater than 1.

A fifth example of the X-ray system, optionally including one or more of the previous examples, further includes where the pin comprises a first brazing separating the pin from a hat, further comprising a second brazing separating the hat from a metallization.

A sixth example of the X-ray system, optionally including one or more of the previous examples, further includes where the high-voltage connector provides a current of 20-80 kHz AC.

A seventh example of the X-ray system, optionally including one or more of the previous examples, further includes where the refractory material comprises a stable oxide layer.

An eighth example of the X-ray system, optionally including one or more of the previous examples, further includes where a diameter of the pin is between 1.5 to 3.0 mm.

A ninth example of the X-ray system, optionally including one or more of the previous examples, further includes where the pin is a single pin of a plurality of pins, wherein the plurality of pins comprises three or more pins.

An embodiment of a system comprises an X-ray system comprising an X-ray tube physically coupled to a high-voltage connector via a plurality of pins, wherein a pin of the plurality of pins comprises niobium.

A first example of the system further includes where the pin or other pins of the plurality of pins comprise tungsten, molybdenum, or tantalum.

A second example of the system, optionally including the first example, further includes where the pin is coated with coating comprising one of gold or platinum, and wherein the coating extends along an entire circumference and width of the pin and blocks a hat comprising nickel-cobalt ferrous alloy or nickel-ferrous alloy from directly contacting the pin.

A third example of the system, optionally including one or more of the previous examples, further includes where the pin is configured to supply a high-frequency alternating current from the high-voltage connector to a cathode of the X-ray tube, wherein the cathode comprises a flat emitter.

A fourth example of the system, optionally including one or more of the previous examples, further includes where the high-frequency alternating current is 20-80 kHz AC, and wherein a ratio of a skin depth of the pin to a pin radius is close to or greater than 1a when conducting the high-frequency alternating current from the high-voltage connector to a flat emitter of the X-ray tube.

A fifth example of the system, optionally including one or more of the previous examples, further includes where the pin comprises a first brazing and a second brazing sandwiching a hat, and wherein a metallization is arranged between the second brazing and a ceramic material, wherein the ceramic material corresponds to a socket in which the pin is arranged.

An embodiment of a connecting device, comprises a plurality of conductive pins fastening a high-voltage connector to an X-ray tube, wherein the pins are configured to conduct current from the high-voltage connector to a flat emitter of a cathode of the X-ray tube, wherein the pins comprise a refractory material including one or more of niobium, molybdenum, and tungsten, and tantalum.

A first example of the connecting device further comprises where the pins are directly brazed to an aluminum oxide insulator.

A second example of the connecting device, optionally including the first example, further comprises where the flat emitter is configured to release electrons in response to receiving current.

A third example of the connecting device, optionally including any of the previous examples, further includes where the pins comprise only one refractory material.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray system, comprising:
an interface configured to couple a high-voltage connector to an X-ray tube via a pin comprising a refractory material.

2. The X-ray system of claim 1, wherein the refractory-material is one or more of niobium, molybdenum, and tungsten.

3. The X-ray system of claim 1, wherein the pin is arranged in a brazed vacuum feedthrough, wherein the pin comprises a hat formed as a single-piece monolith with the pin, wherein the pin and the hat comprise the refractory material.

4. The X-ray system of claim 1, wherein the pin is coated with a coating comprising gold or platinum, and wherein the coating separates the pin from a hat, wherein the hat comprises a nickel-cobalt ferrous alloy or a nickel-ferrous alloy.

5. The X-ray system of claim 4, wherein a ratio of a skin depth of the pin to a pin radius is equal to or greater than 1.

6. The X-ray system of claim 1, wherein the pin comprises a first brazing separating the pin from a hat, further comprising a second brazing separating the hat from a metallization.

7. The X-ray system of claim 1, wherein the high-voltage connector provides a current of 20-80 kHz AC.

8. The X-ray system of claim 1, wherein the refractory material comprises a stable oxide layer.

9. The X-ray system of claim 8, wherein a diameter of the pin is between 1.5 to 3.0 mm.

10. The X-ray system of claim 1, wherein the pin is a single pin of a plurality of pins, wherein the plurality of pins comprises three or more pins.

11. A system, comprising:
an X-ray system comprising an X-ray tube physically coupled to a high-voltage connector via a plurality of pins, wherein a pin of the plurality of pins comprises niobium.

12. The system of claim 11, wherein the pin or other pins of the plurality of pins comprise tungsten, molybdenum, or tantalum.

13. The system of claim 11, wherein the pin is coated with a coating comprising one of gold or platinum, and wherein the coating extends along an entire circumference and width of the pin and blocks a hat comprising a nickel-cobalt ferrous alloy or a nickel-ferrous alloy from directly contacting the pin.

14. The system of claim 11, wherein the pin is configured to supply a high-frequency alternating current from the high-voltage connector to a cathode of the X-ray tube, wherein the cathode comprises a flat emitter.

15. The system of claim 14, wherein the high-frequency alternating current is 20-80 kHz AC, and wherein a ratio of a skin depth of the pin to a pin radius is close to or greater than 1 when conducting the high-frequency alternating current from the high-voltage connector to the flat emitter of the X-ray tube.

16. The system of claim 11, wherein the pin comprises a first brazing and a second brazing sandwiching a hat, and wherein a metallization is arranged between the second brazing and a ceramic material, wherein the ceramic material corresponds to a socket in which the pin is arranged.

17. A connecting device, comprising:
a plurality of conductive pins fastening a high-voltage connector to an X-ray tube, wherein the plurality of conductive pins is configured to conduct current from the high-voltage connector to a flat emitter of a cathode of the X-ray tube, wherein the plurality of conductive pins comprise a refractory material including at least one of niobium, molybdenum, tungsten, and tantalum.

18. The connecting device of claim 17, wherein the conductive pins are directly brazed to an aluminum oxide insulator.

19. The connecting device of claim 17, wherein the flat emitter is configured to release electrons in response to receiving current.

20. The connecting device of claim 17, wherein the conductive pins comprise only one refractory material.

* * * * *